United States Patent [19]

Hummel

[11] Patent Number: 5,188,189
[45] Date of Patent: Feb. 23, 1993

[54] ADJUSTABLE UNIVERSAL DRIVER
[75] Inventor: Scott Hummel, Denville, N.J.
[73] Assignee: Hummel Machine and Tool Company, Kearny, N.J.
[21] Appl. No.: 757,835
[22] Filed: Sep. 11, 1991
[51] Int. Cl.$^5$ ............................................. B25B 23/00
[52] U.S. Cl. ................... 173/213; 81/177.75; 81/177.8
[58] Field of Search ................ 81/57.26, 57.28, 57.45, 81/177.8, 177.6, 177.75; 173/163, 213

[56] References Cited

U.S. PATENT DOCUMENTS

| | | | |
|---|---|---|---|
| 1,239,847 | 9/1917 | Townill . | |
| 1,273,774 | 7/1918 | Golding et al. . | |
| 1,295,072 | 2/1919 | Schanno . | |
| 1,395,436 | 11/1921 | Lawrence | 81/177.75 |
| 1,398,234 | 11/1921 | Landis | 81/177.75 X |
| 1,537,657 | 5/1925 | Bunch | 81/177.75 |
| 2,498,465 | 2/1950 | Thomas . | |
| 2,791,142 | 5/1957 | Lyon | 81/57.26 |
| 3,111,049 | 11/1963 | Brehmer . | |
| 3,835,735 | 9/1974 | Carr . | |
| 4,947,942 | 8/1990 | Lightle et al. . | |

Primary Examiner—Frank T. Yost
Assistant Examiner—Rinaldi Rada
Attorney, Agent, or Firm—Amster, Rothstein & Ebenstein

[57] ABSTRACT

An adjustable universal driver useful in driving screws, drilling holes or the like, includes a sleeve unit having a sleeve linkage connecting linking ends of a grip sleeve and a nose sleeve to permit pivoting of one of the sleeves relative to the other about a transverse axis of the sleeve linkage; a drive shaft unit having a universal joint operatively connecting a driven end of a grip shaft and a driving end of a nose shaft for rotation as a drive shaft unit relative to the sleeve unit; and means for adjusting and retaining the angle formed by the nose sleeve and nose shaft relative to the grip sleeve and grip shaft.

12 Claims, 6 Drawing Sheets

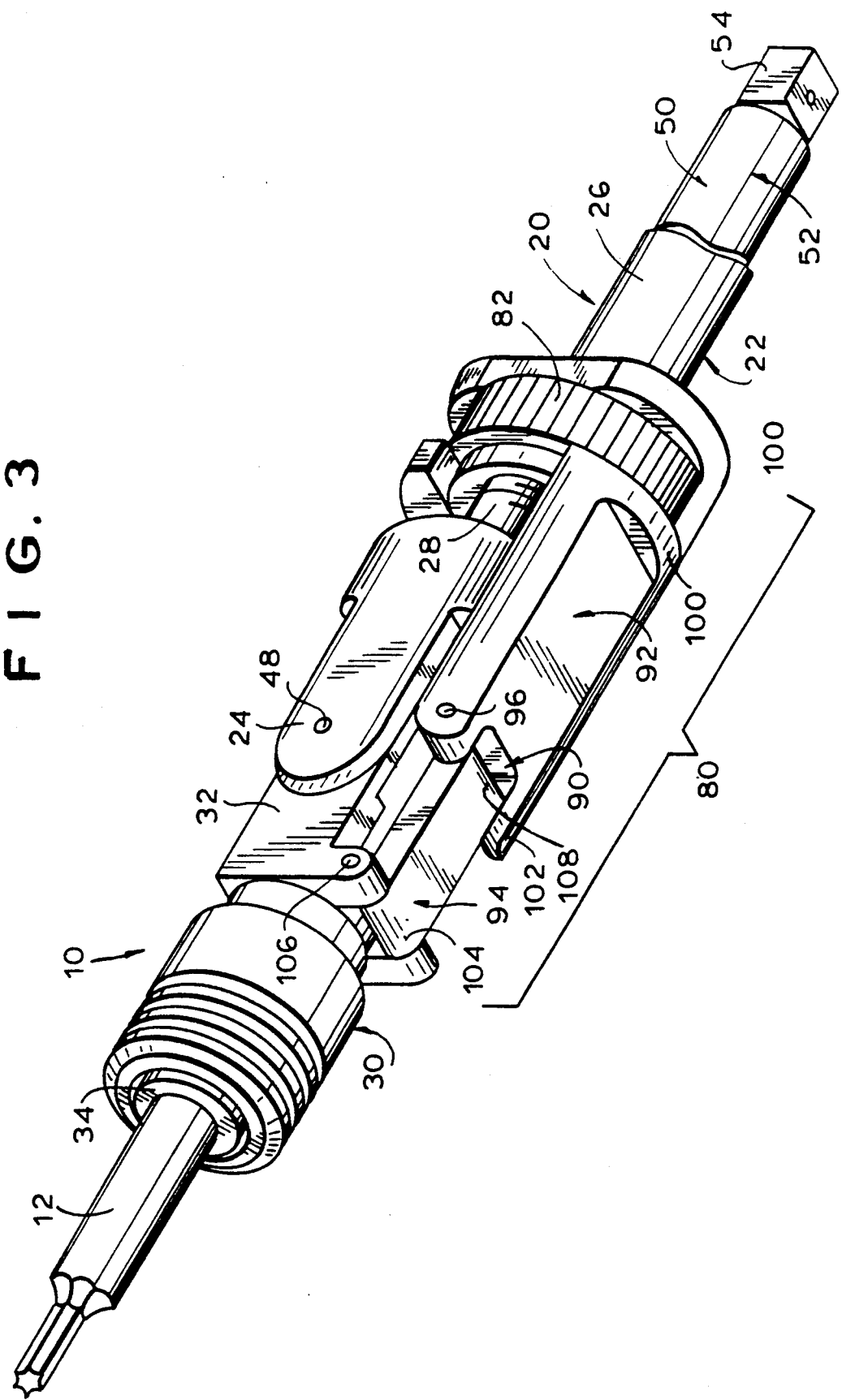

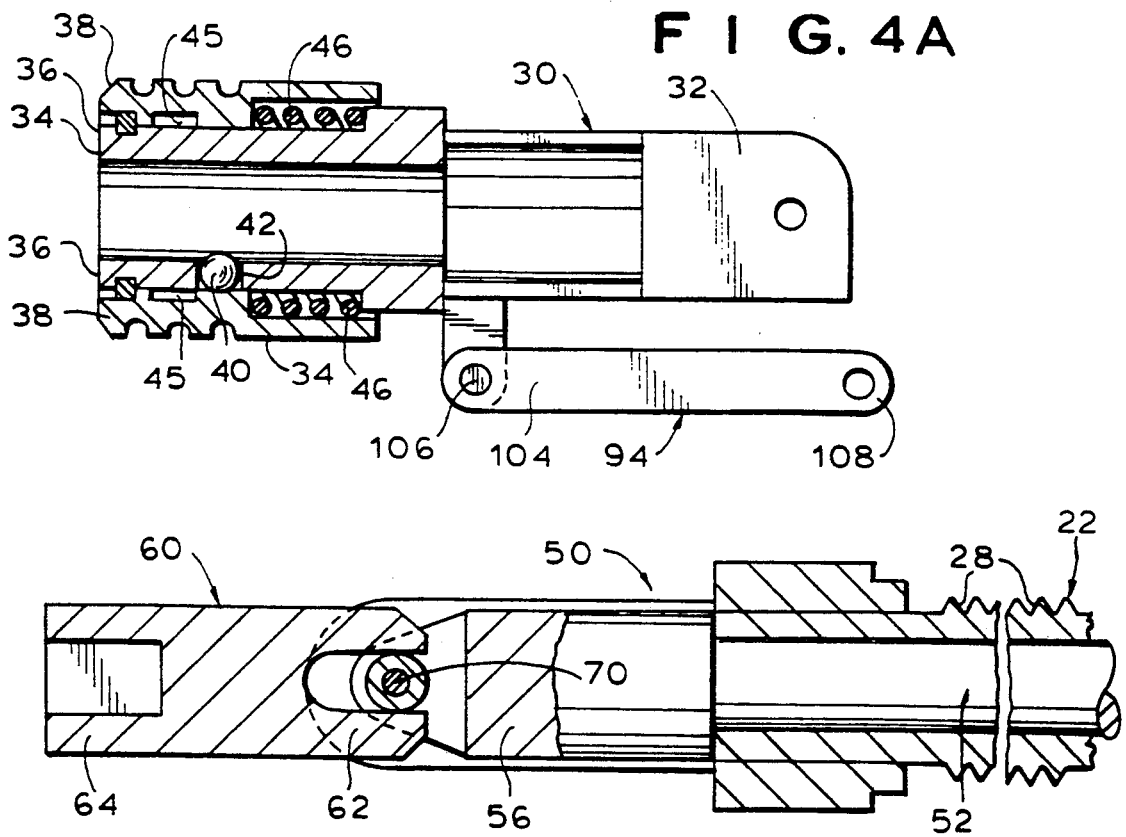
FIG. 4A
FIG. 4B
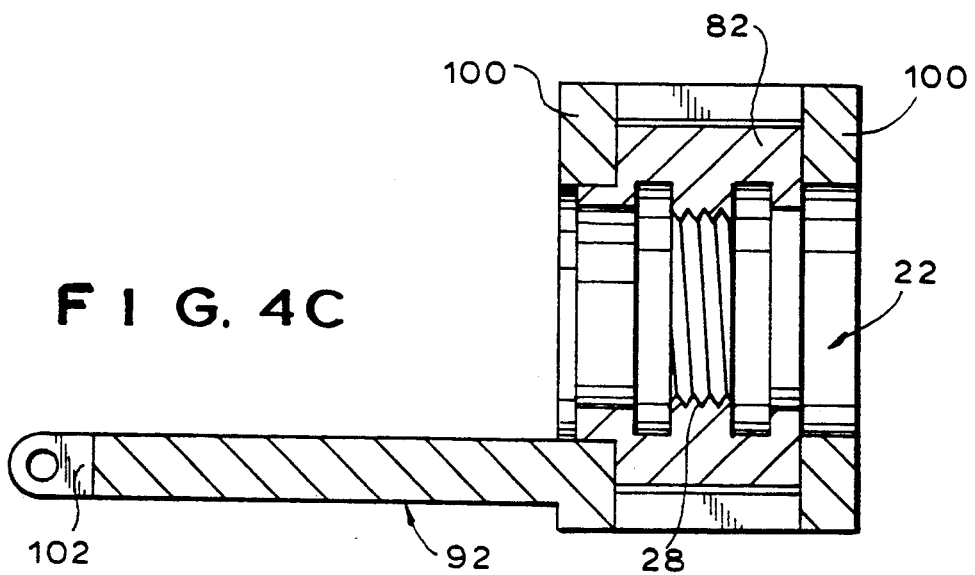
FIG. 4C

ADJUSTABLE UNIVERSAL DRIVER

BACKGROUND OF THE INVENTION

The present invention relates to an adjustable universal driver, and more particularly to an adjustable universal driver useful in driving screws, drilling holes or the like in a surgical environment.

Adjustable universal drivers are well known in the mechanical tool art for driving a first shaft by a second shaft where the first and second shafts are disposed end to end at an obtuse angle. Indeed, such drivers have been developed for the surgical field as well, as exemplified in U.S. Pat. No. 4,947,942. The known devices, both in the medical and non-medical fields, have not proven to be entirely satisfactory in use.

In the conventional drivers, the ability of the drive shaft unit (containing the universal joint) to rotate within the sleeve unit without binding degraded as the device was changed from the linear orientation (that is, when the axis of the nose shaft and sleeve are aligned with the axis of the grip shaft and sleeve) to an orientation in which the driver assumed an angle (that is, the axis of the nose shaft and sleeve forms a non-linear angle with the axis of the grip shaft and sleeve). Such binding, when it occurred, interfered with the free rotation of the drive shaft unit within the sleeve unit, thereby rendering the driver unable to perform its intended function.

A further disadvantage of the conventional drivers is that the angle formed between the axes of the nose and grip ends of the device was either unfixed (that is, the nose end could pivot freely about the grip end), was manually maintained (that is, the mechanism used to pivot the nose end relative to the grip end had to be manually maintained once the desired angular disposition was achieved), or required a separate manual fixation (that is, once the proper angle between the nose and grip ends was achieved, a special mechanism had to be actuated in order to fix the angle).

While aforenoted disadvantages of the conventional drivers apply to such devices whether employed in the surgical or non-surgical field, they are especially significant in the surgical field where the drilling of a hole or the driving of a screw may be required at a very specific angle, and where the surgeon has neither the time to apply a separate fixation mechanism once the desired angle has been achieved or the spare hand or fingers which may be required in order to manually maintain the desired angle once achieved.

Accordingly, it is an object of the present invention to provide an adjustable universal driver wherein the nose and grip ends may be disposed and maintained at a predetermined angle without the user thereof having to manually maintain the angle or actuate a separate mechanism for maintaining the angle.

Another object is to provide such a driver wherein there is no binding between the drive shaft unit and the sleeve unit, regardless of the obtuse angle formed between the grip and nose ends.

A further object is to provide such a drive which is of simple and economical construction, easy to maintain and easy to use.

SUMMARY OF THE INVENTION

It has now been found that the above and related objects of the present invention are obtained in an adjustable universal driver useful in driving screws, drilling holes or the like, comprising a sleeve unit, a drive shaft unit and adjusting means. The sleeve unit includes a hollow grip sleeve having a linking end and a free end, a hollow nose sleeve having a linking end and a free end, and sleeve linkage means connecting the linking ends of the grip sleeve and the nose sleeve to permit pivoting of one of the sleeves relative to the other of the sleeves about a transverse axis of the sleeve linkage means. The drive shaft unit is rotatable relative to the sleeve unit and includes a grip shaft extending at least partially through the grip sleeve and being rotatable relative thereto, the grip shaft defining a driving end adapted to be rotated and a driven end, a rotatable nose shaft extending at least partially through the nose sleeve, the nose shaft defining a driving end and a driven end, and a universal joint operatively connecting the driven end of the grip shaft and the driving end of the nose shaft for rotation as a drive shaft unit relative to the sleeve unit. The adjusting means adjusts and retains the angle formed by the nose sleeve and nose shaft relative to the grip sleeve and grip shaft.

In a preferred embodiment the grip sleeve includes a threaded portion between the grip sleeve ends, and the adjusting means includes a threaded knob and a linkage assembly. The threaded knob is coaxially disposed on and in threaded engagement with the threaded portion of the grip sleeve so that rotation of the knob relative to the grip sleeve causes axial movement of the knob relative to the grip sleeve. The linkage assembly comprises a grip linkage having one end operatively connected to the knob for axial movement therewith and a linkage end, a nose linkage having one end pivotally connected to the nose sleeve at a fixed point along the axis thereof and a linkage end, and adjustment linkage means pivotally connecting the linkage ends of the grip linkage and nose linkage. Rotation of the knob results in a variation of the angle formed by the nose sleeve and nose shaft relative to the grip sleeve and grip shaft. Preferably the one end of the grip linkage of the linkage assembly is operatively connected to the knob for axial movement in both directions, typically by abutting the knob on both sides thereof, and the linkage assembly is non-rotatable relative to the sleeve unit.

Ideally, the sleeve linkage means is always disposed along the length of the drive shaft unit opposite the universal joint (at the intersection of the two orthogonal axes of the universal joint), in transverse alignment with the universal joint.

Preferably the linking ends of the grip sleeve and the nose sleeve substantially overlap, the driven end of the nose shaft is adapted to releasably receive a bit for rotation therewith, and the universal joint permits relative angular movement of the grip shaft and the nose shaft about two orthogonal axes within the universal joint.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein:

FIG. 3 is a fragmentary isometric view thereof taken from the bottom;

FIG. 4A is a side elevational view of the nose sleeve, partially in cross section;

FIG. 4B is a fragmentary side elevational view of the drive shaft unit, partially in cross section;

FIG. 4C is a side elevational view of the grip sleeve and knob, partially in cross section;

PREFERRED EMBODIMENTS OF THE PRESENT INVENTION

Figure 1:
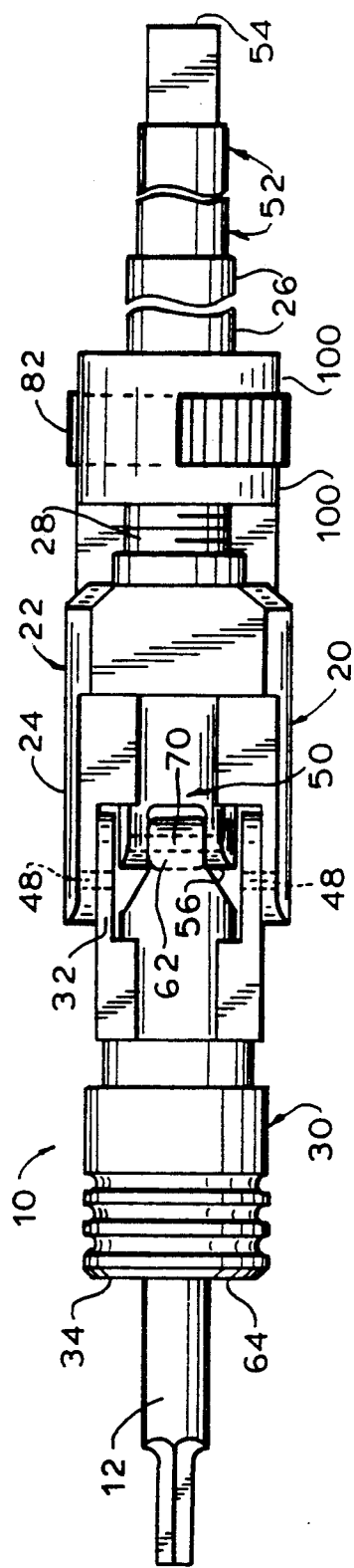
FIG. 1 is a fragmentary top plan view of an adjustable universal driver according to the present invention with the nose and grip ends forming a linear angle.
Figure 2:
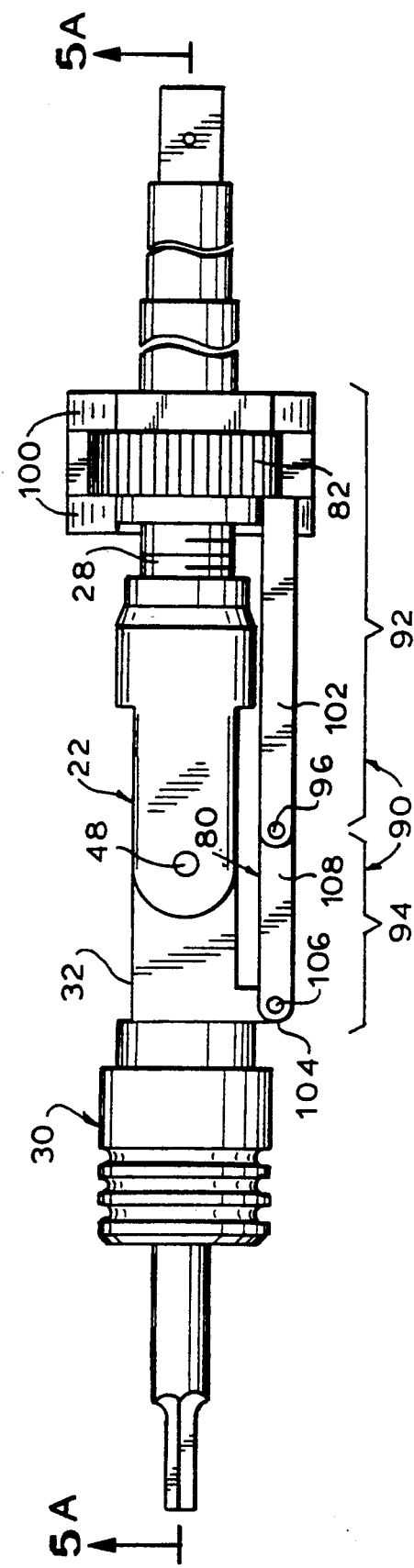
FIG. 2 is a fragmentary side elevational view thereof.

Referring now to FIGS. 1-3, therein illustrated is an adjustable universal driver according to the present invention, generally designated by the reference numeral 10. Depending upon the nature of the bit 12 used in association with the driver 10, the driver may be useful for driving screws, drilling holes or the like. The entire unit, including the bit, is preferably formed of stainless steel or a like rigid, surgical metal capable of withstanding the rigors of sterilization. The materials from which the driver is constructed will depend upon the intended end-application thereof. Thus while surgical steel or chrome is especially preferred for drivers intended for use in surgical applications, less expensive materials may be employed for non-surgical applications.

The driver 10 is formed basically of three components: a sleeve unit; a drive shaft unit; and means for adjusting and retaining the angle formed between the forward or nose end of the driver and the rear or grip end of the driver.

The Sleeve Unit

More particularly, the sleeve unit, generally designated 20, includes a hollow grip sleeve 22 having a linking end 24 and a free end 26. Intermediate the free end 26 and the linking end 24, the grip sleeve 22 defines an externally threaded portion 28, for reasons which will become apparent hereinafter. The linking end 24 of the grip sleeve 22 is bifurcated and enlarged relative to the remainder of the grip sleeve 22.

The sleeve unit 20 also includes a hollow nose sleeve generally designated 30 having a linking end 32 and a free end 34. The linking end 32 of the nose sleeve 30 is bifurcated, like the linking end 24 of the grip sleeve 22, with the end panels of the grip sleeve linking end 24 overlapping the end panels of the nose sleeve linking end 32.

Figure 5A:
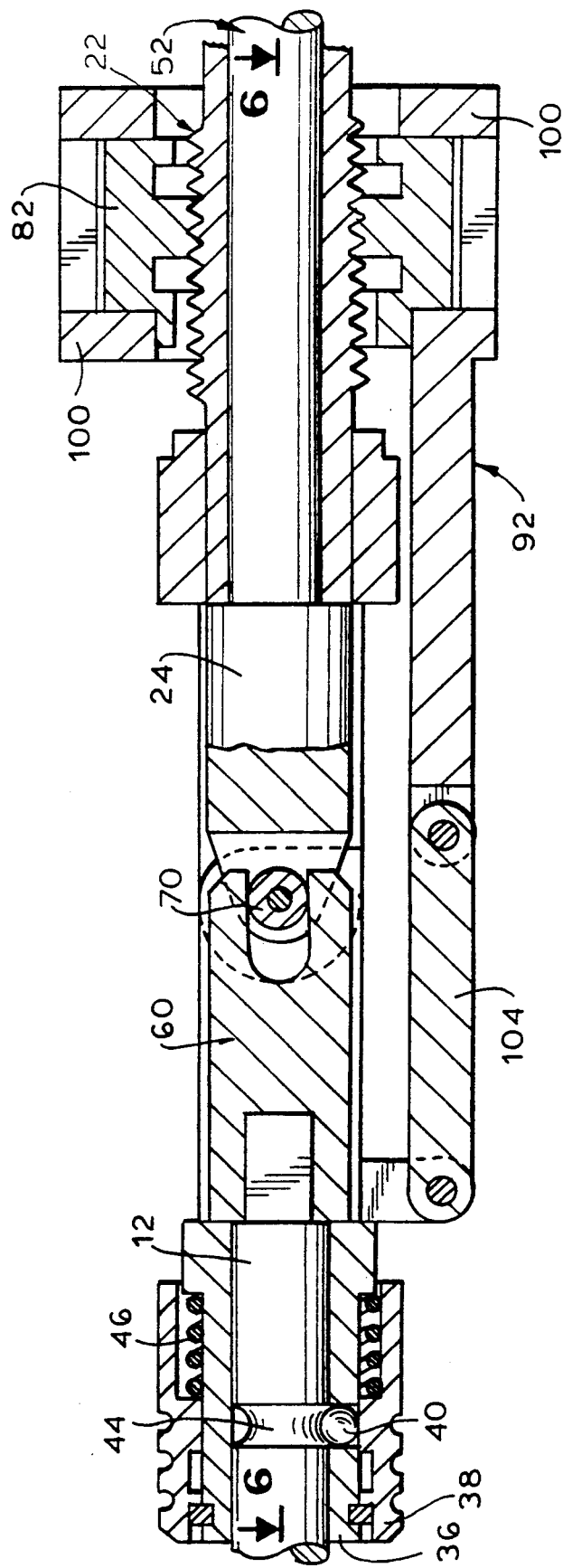
FIG. 5A is a fragmentary sectional view taken along the line 5A—5A of FIG. 2.
Figure 5B:
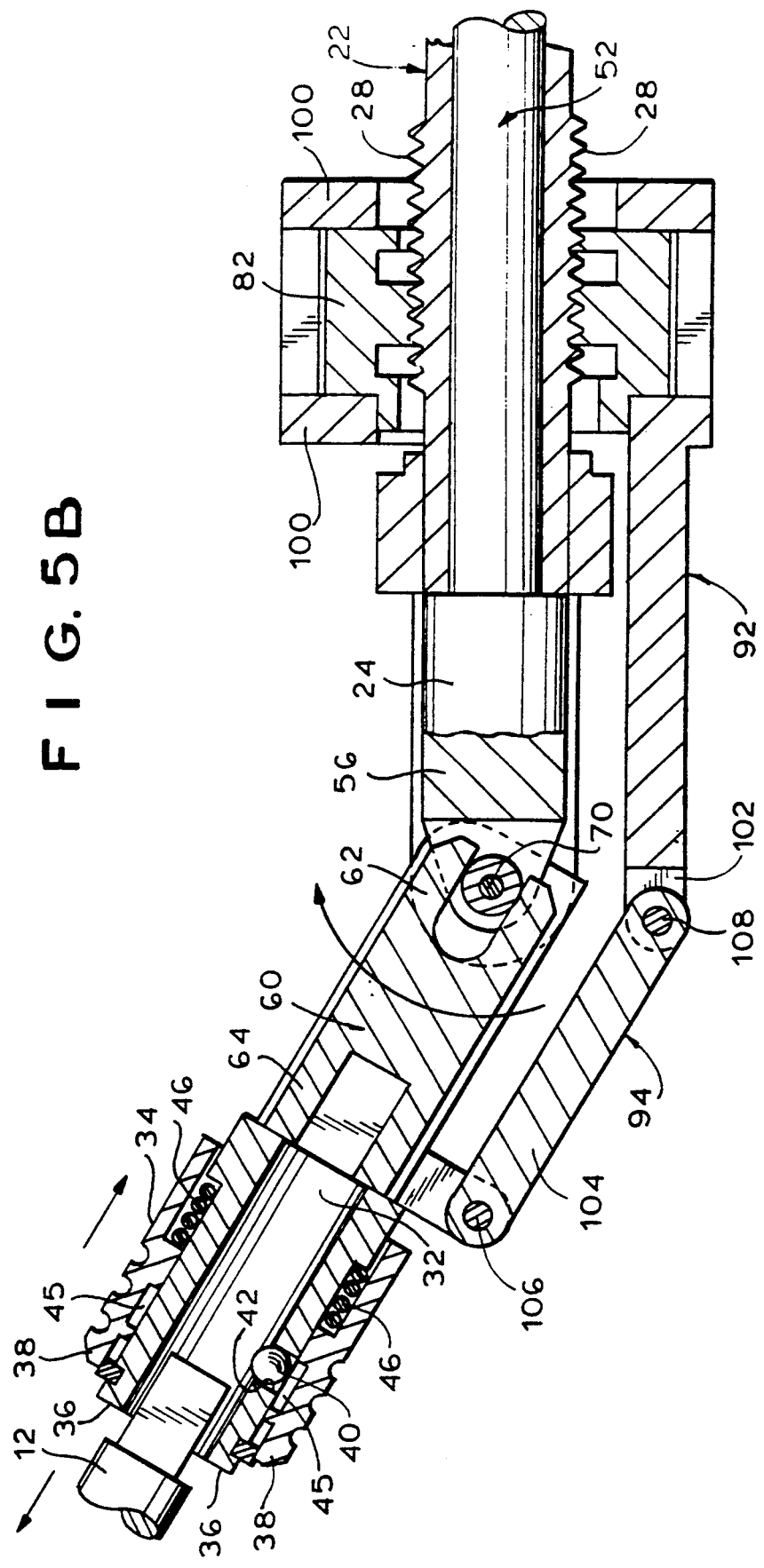
FIG. 5B is a sectional view similar to FIG. 5A but showing the nose and grip disposed at an obtuse angle, the nose sleeve also being partially retracted to enable replacement of a bit.
Figure 6:
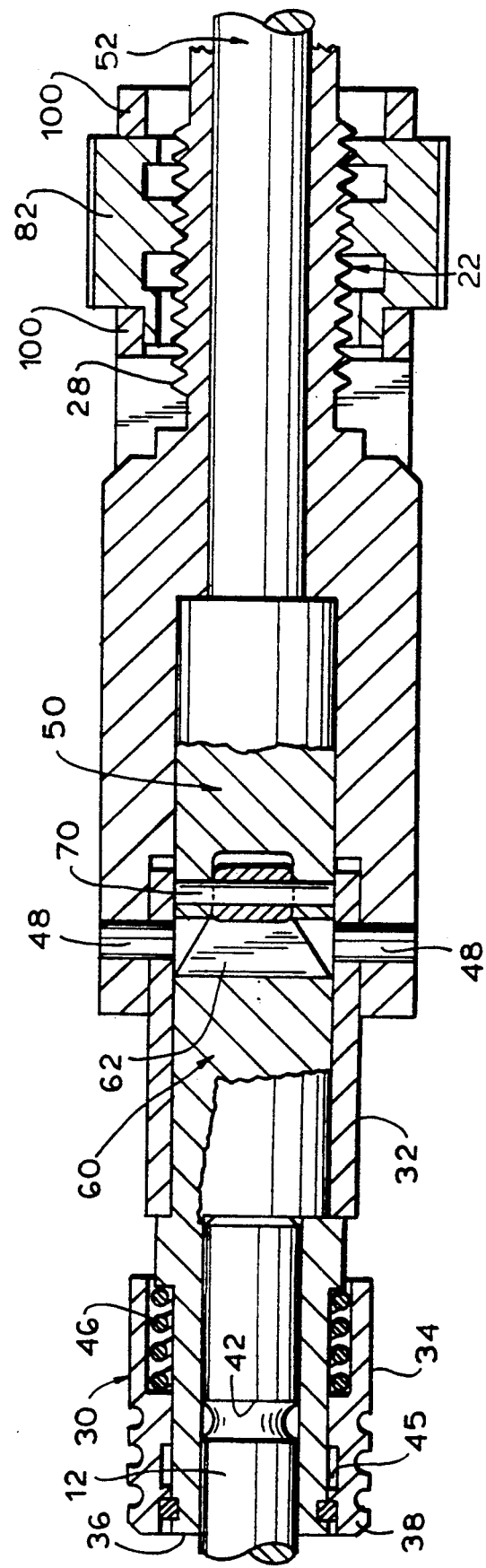
FIG. 6 is a fragmentary sectional view taken along the line 6—6 of FIG. 5A.

As best seen in FIG. 4A, the nose sleeve free end 32 includes a releasable locking mechanism for receiving therein a bit 12 (not shown in FIG. 4A), including an inner cylinder 36, an outer cylinder 38, and a ball 40 disposed at least partially in a recess 42 in the inner cylinder 36. Referring now also to FIG. 5A, the ball 40 normally extends inwardly from the inner side wall of cylinder 36 and occupies in part a circumferential groove 44 in the bit 12, the inner wall of the outer cylinder 38 precluding retreat of the ball 40 from the groove 44 and thereby causing retention of the bit 12 within the nose sleeve free end 32. On the other hand, when the outer sleeve 38 is manually retracted against the grip or linking end 32 of the nose sleeve 30, as illustrated in FIG. 5B, a recess 45 in the inner surface of the outer sleeve 38 permits the ball 40 to retreat from the bit groove 44, thus allowing removal and replacement of the bit 12. Once the outer sleeve 38 is released, biasing means 46, such as a spring disposed intermediate the inner and outer cylinders 36, 38, returns outer cylinder 38 to its normal position, where it precludes separation of the bit 12 from the nose sleeve 30.

Sleeve linkage means 48, typically a common pivot pin, connects the linking ends 24, 32 of the grip sleeve 22 and the nose sleeve 30 to permit pivoting of one of the sleeves 22, 30 relative to the other of the sleeves 30, 22 about the axis of the sleeve linkage means 48, which extends transverse to the major axis of the sleeve unit 20. Thus the sleeve linkage means 48 enables pivoting of the grip sleeve 22 and nose sleeve 30 relative to one another about the axis of the sleeve linkage means 48.

The Drive Shaft Unit

Referring also to FIG. 4B, the drive shaft unit, generally designated 50, which is rotatable relative to the sleeve unit 20, includes a grip shaft, generally designated 52, extending at least partially through the grip sleeve 22 and being rotatable relative thereto. The grip shaft 52 defines a driving end 54 adapted to be rotated and a driven end 56 (see FIG. 1). The driving end 54 is illustrated as squared off to facilitate linkage with mechanical means for rotating the grip shaft 52. However, where it is intended that the grip shaft 52 be manually rotated, the driving end 54 may be an enlarged, knurled portion to facilitate gripping and rotation thereof.

The drive shaft unit 50 also includes a nose shaft, generally designated 60, extending at least partially through the nose sleeve 30 and being rotatable relative thereto. The nose shaft 60 defines a driving end 62 and a driven end 64 (see FIG. 4B). While the illustrated embodiment has a short driven end 64 which terminates within the nose sleeve 30 to facilitate the insertion or removal of bits 12 therefrom, where the nose shaft driven end 64 is itself configured to act as a tool (being shaped, for example, as a screw driver tip, a cutting tip, or the like), the nose shaft driven end 64 will project outwardly beyond the end of the nose sleeve 30.

The driven end 56 of the grip shaft 52 and the driving end 62 of the nose shaft 60 define and are joined by a universal joint 70, the universal joint 70 operatively connecting the driven end 56 and the driving end 62 for rotation as a drive shaft unit 50 relative to the sleeve unit 20. Thus, the nose end of the device, including the nose sleeve 30 and nose shaft 60 (and any bit 12 attached thereto), is pivotable relative to the grip end of the device, including the grip sleeve 22 and grip shaft 52, about the axis of the sleeve linkage means 48. Accordingly the axes of the nose end and grip end may define a linear angle (i.e., a straight line) as illustrated in FIGS. 1-3, 5A and 6, or any of a variety of obtuse angles as illustrated in FIG. 5B.

The Adjusting Means

Finally, referring now also to FIGS. 4A and 4C, the driver 10 of the present invention includes means, generally designated 80, for adjusting and retaining the angle formed by the nose end (that is, the nose sleeve 30 and nose shaft 60) relative to the grip end (that is, the grip sleeve 22 and grip shaft 52). More particularly, the adjusting means 80 includes a threaded knob 82 coaxially disposed on and in threading engagement with the externally threaded portion 28 of the grip sleeve 22 so that rotation of the knob 82 relative to the grip sleeve threaded portion 28 causes axial movement of the knob 82 relative to the grip sleeve 22 along the grip sleeve axis.

The adjusting means 80 additionally includes a linkage assembly 90 comprising a grip linkage generally designated 92, a nose linkage generally designated 94, and adjusting linkage means 96 pivotably connecting the grip linkage 92 and the nose linkage 94. More particularly, the grip linkage 92 has one end 100 operatively connected to the knob 82 for axial movement therewith, and a linkage end 102. The grip linkage end 100 operatively connected to the knob 82 for axial movement is bifurcated and extends to either side of the knob 82 so that the end 100 is operatively connected to the knob 82 by abutting the knob 82 on both sides thereof. The nose linkage 94 has one end 104 pivotably connected at 106 (e.g., by a pivot pin) to the nose sleeve 32 at a fixed point along the axis thereof and a linkage end 108. The adjusting linkage means 96, such as a pivot pin, pivotably connects the linkage ends 102, 108 of the grip linkage 92 and the nose linkage 94.

Accordingly, rotation of the knob 82 about the threaded portion 28 of the grip sleeve 22 causes the traverse of the knob 82 in one direction or another along the axis of the grip sleeve 22. As the knob 82 travels up and down the axis, it carries with it the grip linkage 92, which is operatively connected by the bifurcated end 100 to the knob 82 for axial movement therewith. On the other hand, the nose sleeve 32, which is connected to the grip linkage 92 by the adjusting linkage means 96 and the nose linkage 94, cannot move axially relative to the nose sleeve 32 and thus can respond only by moving angularly (i.e., moving about the pivot 48), thus varying the angle formed by the nose end and the grip end.

The linkage assembly 90 is non-rotatable relative to the sleeve unit 20, being fixed in a non-rotatable manner at the upper and lower ends thereof (that is, to the upper or grip end by the grip linkage end 100 secured to the grip sleeve 22 and at the lower or nose end by the nose linkage end 104 pivotably secured to the nose sleeve 32).

It will be appreciated that, as a result of the unique construction of the device, the sleeve linkage means 48 is always disposed along the length of the drive shaft unit 50 opposite the universal joint 70 thereof—in other words, in transverse alignment with the universal joint 70 at the intersection of the two orthogonal axes of the universal joint. This construction has the advantage that there is no binding as the knob 82 is rotated since the sleeve linkage means 48 and universal joint 70 are always disposed at the same point along the length of the driver 10.

The control of the angle formed by the nose and grip ends of the driver by the rotatable threaded knob 82 affords numerous advantages not found in conventional drivers. First, because the angle is varied by a threaded engagement (i.e., rotation of a knob), the precisely desired angle may be easily and rapidly achieved with more precision than would be the case if one were simply directly manually moving the ends of the driver. Second, the angle, once formed by suitable rotation of the knob is retained automatically by the threaded engagement so long as is there is no further rotation of the knob. In other words, the surgeon need not take any special action to maintain the angle achieved or even to set a special mechanism for fixing the angle achieved; the natural resistance of the knob to rotation due to attempts to change the angle through manipulation of the ends of the driver suffices to maintain the desired angle once achieved. Third, the angle can easily be made reproducible by suitable marking of the knob so that it can be returned to its original orientation at a later time.

To summarize, the present invention provides an adjustable universal driver wherein the nose and grip ends may be disposed and maintained at a predetermined angle without the user thereof having to manually maintain the angle or actuate a separate mechanism for maintaining the angle. Further, there is no binding between the drive shaft unit and the sleeve unit, regardless of the obtuse angle formed between the grip and nose ends. Finally, the driver is of a simple and economical construction, easy to maintain and easy to use.

Now that the preferred embodiments of the present invention have been shown and described in detail, various modifications and improvements thereon will become readily apparent to those skilled in the art. Accordingly, the spirit and scope of the present invention is to be construed broadly and in a manner consistent with the appended claims, and not limited by the foregoing specification.

I claim:

1. An adjustable universal driver useful in transmitting rotary motion useful for driving screws and drilling holes, comprising:
    (A) a sleeve unit including:
        (i) a hollow grip sleeve having a linking end and a free end,
        (ii) a hollow nose sleeve having a linking end and a free end, and
        (iii) sleeve linkage means connecting said linking ends of said grip sleeve and said nose sleeve to permit pivoting of one of said sleeve relative to the other of said sleeves about a transverse axis of said sleeve linkage means;
    (B) a drive shaft unit rotatable relative to said sleeve unit, including:
        (i) a grip shaft extending at least partially through said grip sleeve and being rotatable relative thereto, said grip shaft defining a driving end adapted to be rotated and a driven end,
        (ii) a nose shaft extending at least partially through said nose sleeve and being rotatable relative thereto, said nose shaft defining a driving end and a driven end, and
        (iii) a single universal joint operatively connecting said driven end of said grip shaft and said driving end of said nose shaft for rotation as a drive shaft unit relative to said sleeve unit; and
    (C) means for adjusting and retaining the angle formed by said nose sleeve and nose shaft relative to said grip sleeve and grip shaft, said adjusting and retaining means including a rotatable member for actuating the adjusting of the angle by rotation of said rotatable member.

2. The driver of claim 1 wherein said sleeve linkage means is always disposed in a plane transverse to the length of said sleeve unit and passing through said universal joint.

3. The driver of claim 2 wherein said sleeve linkage means is always disposed substantially in alignment along the transverse axis of said universal joint.

4. The driver of claim 2 wherein said universal joint enables pivoting about two orthogonal axes thereof, and said sleeve linkage means is always disposed along the length of said sleeve unit in a plane passing through both orthogonal axes of said universal joint.

5. The driver of claim 1 wherein said linking ends of said grip sleeve and said nose sleeve substantially overlap.

6. The driver of claim 1 wherein said driven end of said nose shaft is adapted to releasably receive a bit for rotation therewith.

7. The driver of claim 1 wherein said universal joint permits relative angular movement of said grip shaft and said nose shaft about two orthogonal axes within said universal joint.

8. An adjustable universal driver useful in transmitting rotary motion, comprising:
   (A) a longitudinally-extending sleeve unit including:
      (i) a hollow grip sleeve having a linking end, a free end, and a threaded portion therebetween,
      (ii) a hollow nose sleeve having a linking end and a free end, and
      (iii) sleeve linkage means connecting said linking ends of said grip sleeve and said nose sleeve to permit pivoting of one of said sleeves relative to the other end of said sleeves about a transverse axis of said sleeve linkage means;
   (B) a longitudinally-extending drive shaft unit rotatable relative to said sleeve unit, including:
      (i) a grip shaft extending at least partially through said grip sleeve and being rotatable relative thereto, said grip shaft defining a driving end adapted to be rotated and a driven end,
      (ii) a nose shaft extending at least partially through said nose sleeve and being rotatable relative thereto, said nose shaft defining a driving end and a driven end, and
      (iii) a universal joint operatively connecting said driven end of said grip shaft and said driving end of said nose shaft for rotation as said drive shaft unit relative to said sleeve unit; and
   (C) means for adjusting and retaining the angle formed by said nose sleeve and nose shaft relative to said grip sleeve and grip shaft, including:
      (i) a threaded knob coaxially disposed on and in threaded engagement with said threaded portion of said grip sleeve so that rotation of said knob relative to said grip sleeve causes axial movement of said knob relative to said grip sleeve, and
      (ii) a longitudinally-extending linkage assembly comprising (a) a grip linkage having one end operatively connected to said knob for axial movement therewith and a linkage end, (b) a nose linkage having one end pivotally connected to said nose sleeve at a fixed point along the axis thereof and a linkage end, and (c) adjusting linkage means pivotally connecting said linkage ends of said grip linkage and nose linkage;
   whereby rotation of said knob results in a variation of said angle formed by said nose sleeve and nose shaft relative to said grip sleeve and grip shaft.

9. The driver of claim 8 wherein said one end of said grip linkage of said linkage assembly is operatively connected to said knob for axial movement in both directions along the longitudinal axis.

10. The driver of claim 9 wherein said one end of said grip linkage of said linkage assembly is operatively connected to said knob by abutting said knob on both sides thereof.

11. The driver of claim 8 wherein said linkage assembly is non-rotatable relative to said sleeve unit.

12. An adjustable universal driver useful in transmitting rotary motion, comprising:
   (A) a longitudinally-extending sleeve unit including:
      (i) a hollow grip sleeve having a linking end, a free end, and a threaded portion intermediate said grip sleeve ends,
      (ii) a hollow nose sleeve having a linking end and a free end, and
      (iii) sleeve linkage means connecting said linking ends of said grip sleeve and said nose sleeve with said linking ends substantially overlapping to permit pivoting of one of said sleeves relative to the other of said sleeves about a transverse axis of said sleeve linkage means;
   (B) a longitudinally-extending drive shaft unit rotatable relative to said sleeve unit, including:
      (i) a grip shaft extending at least partially through said grip sleeve and being rotatable relative thereto, said grip shaft defining a driving end adapted to be rotated and a driven end,
      (ii) a rotatable nose shaft extending at least partially through said nose sleeve and being rotatable relative thereto, said nose shaft defining a driving end and a driven end, and
      (iii) a universal joint operatively connecting said driven end of said grip shaft and said driving end of said nose shaft for rotation as said drive shaft unit relative to said sleeve unit, said universal joint enabling relative angular movement of said grip shaft and said nose shaft about two orthogonal axes within said universal joint, said sleeve linkage means being always disposed along the length of said sleeve unit opposite said universal joint at the intersection of the two orthogonal axes of said universal joint and in alignment along a transverse axis with said universal joint; and
   (C) means for adjusting and retaining the angle formed by said nose sleeve and nose shaft relative to said grip sleeve and grip shaft, including:
      (i) a threaded knob coaxially disposed on and in threaded engagement with said threaded portion of said grip sleeve so that rotation of said knob relative to said grip sleeve causes axial movement of said knob relative to said grip sleeve, and
      (ii) a longitudinally-extending linkage assembly which is non-rotatable relative to said sleeve unit, comprising (a) a grip linkage having one end operatively connected to said knob by abutment on both sides thereof for axial movement therewith in both directions along the longitudinal axis and a linkage end, (b) a nose linkage having one end pivotally connected to said nose sleeve at a fixed point along the longitudinal axis thereof and a linkage end, and (c) adjusting linkage means pivotally connecting said linkage ends of said grip linkage and nose linkage;
   whereby rotation of said knob results in a variation of said angle formed by said nose sleeve and nose shaft relative to said grip sleeve and grip shaft.

* * * * *